(12) United States Patent
Park et al.

(10) Patent No.: US 6,916,958 B2
(45) Date of Patent: Jul. 12, 2005

(54) AMINOBIGUANIDES AND THE USE THEREOF TO DISINFECT CONTACT LENSES AND PRESERVE PHARMACEUTICAL COMPOSITIONS

(75) Inventors: Joonsup Park, Arlington, TX (US); Nissanke L. Dassanayake, Arlington, TX (US); Nathaniel D. McQueen, Arlington, TX (US); Ronald L. Schlitzer, Fort Worth, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 10/672,465

(22) Filed: Sep. 26, 2003

(65) Prior Publication Data

US 2004/0063791 A1 Apr. 1, 2004

Related U.S. Application Data

(62) Division of application No. 09/581,952, filed as application No. PCT/US98/27332 on Dec. 18, 1998, now Pat. No. 6,664,294.
(60) Provisional application No. 60/068,330, filed on Dec. 19, 1997.

(51) Int. Cl.$^7$ ............................................. C07C 279/26
(52) U.S. Cl. ...................................................... 564/233
(58) Field of Search ......................................... 564/233

(56) References Cited

U.S. PATENT DOCUMENTS

| 3,270,036 | A | * | 8/1966 | Bernstein et al. ........... 564/233 |
| 3,808,224 | A | | 4/1974 | Aron-Samuel |
| 4,407,791 | A | | 10/1983 | Stark |
| 4,438,011 | A | | 3/1984 | Howes |
| 4,537,746 | A | | 8/1985 | Ogunibiyi et al. |
| 5,185,337 | A | | 2/1993 | Fujii et al. |
| 5,262,411 | A | | 11/1993 | Shirasaka et al. |
| 5,376,686 | A | | 12/1994 | Ishikawa et al. |
| 5,453,435 | A | | 9/1995 | Raheja et al. |
| 5,627,214 | A | | 5/1997 | Schafer et al. |
| 5,631,005 | A | | 5/1997 | Dassanayake et al. |
| 5,900,213 | A | | 5/1999 | Dassanayake et al. |

FOREIGN PATENT DOCUMENTS

| CA | 2098472 | 12/1993 |
| EP | 0 126 567 A1 | 11/1984 |
| EP | 0 456 093 A | 11/1991 |
| EP | 0 507 317 A | 10/1992 |
| EP | 0 575 290 A | 12/1993 |
| GB | 1351025 | 4/1974 |
| WO | WO 87/00437 | 1/1987 |
| WO | WO 99/32158 | 7/1999 |

OTHER PUBLICATIONS

Database CAPLUS on STN, Acc. No. 1969:438919, Noel et al., Comptes Rendus des Seances de L'Academie des Sciences, Serie C: Sciences Chimiques (1969), 268(15), p. 1407–9 (abstract).*

Tanzer et al., "Structural Requirements of Guanide, Biguanide, and Bisbiguanide Agents for Antiplaque Activity", *Antimicrobial Agents and Chemotherapy*, pp. 721–729 (Dec. 1977).

Gilbert, et al., "Synergism Within Polyhexamethylene Biguanide Biocide Formulations", *Journal of Applied Bacteriology* vol. 69, pp. 593–598; (1990).

* cited by examiner

*Primary Examiner*—Brian J. Davis
(74) *Attorney, Agent, or Firm*—Gregg C. Brown

(57) ABSTRACT

Aminobiguanides and the use of same as antimicrobial agents in pharmaceutical compositions are disclosed. The aminobiguanides are useful in the preservation of pharmaceutical compositions, particularly ophthalmic pharmaceutical compositions and compositions for treating contact lenses. The compounds are especially useful for disinfecting contact lenses.

4 Claims, No Drawings

AMINOBIGUANIDES AND THE USE THEREOF TO DISINFECT CONTACT LENSES AND PRESERVE PHARMACEUTICAL COMPOSITIONS

CLAIM FOR PRIORITY

The present application is a divisional of U.S. patent application Ser. No. 09/581,952 now U.S. Pat. No. 6,664,294 filed Aug. 3, 2000, which is a 371 of International Patent Application Serial No. PCT/US98/27332, filed Dec. 18, 1998; which claims priority from U.S. Provisional Application Ser. No. 60/068,330 filed Dec. 19, 1997.

BACKGROUND OF THE INVENTION

The present invention is directed to aminobiguanides having antimicrobial activity, and to the use of these aminobiguanides in pharmaceutical compositions. More specifically, the invention is directed to use of the subject aminobiguanides in compositions and methods for disinfecting contact lenses, and to the use of these compounds to preserve various types of pharmaceutical compositions from microbial contamination, particularly ophthalmic and otic pharmaceutical compositions.

Contact lenses are exposed to a broad spectrum of microbes during normal wear and become soiled relatively quickly. Routine cleaning and disinfecting of the lenses are therefore required. Although the frequency of cleaning and disinfecting may vary somewhat among different types of lenses and lens care regimens, daily cleaning and disinfecting is normally required. Failure to clean and disinfect the lens properly can lead to a multitude of problems ranging from mere discomfort when the lenses are being worn to serious ocular infections. Ocular infections caused by particularly virulent microbes, such as *Pseudomonas aeruginosa,* can lead to loss of the infected eye(s) if left untreated or if allowed to reach an advanced stage before treatment is initiated. It is therefore extremely important that patients disinfect their contact lenses in accordance with the regimen prescribed by their optometrist or ophthalmologist.

Unfortunately, patients frequently fail to follow the prescribed regimens. Many patients find regimens to be difficult to understand and/or complicated, and as a result do not comply with one or more aspects of the regimen. Other patients may have a negative experience with the regimen, such as ocular discomfort attributable to the disinfecting agent, and as a result do not routinely disinfect their lenses or otherwise stray from the prescribed regimen. In either case, the risk of ocular infections is exacerbated.

Despite the availability of various types of contact lens disinfecting systems, such as heat, hydrogen peroxide, and other chemical agents, there continues to be a need for improved systems which: 1) are simple to use, 2) have potent antimicrobial activity, and 3) are nontoxic (i.e., do not cause ocular irritation as the result of binding to the lens material). There is also a need for chemical disinfecting agents that retain their antimicrobial activity in the presence of salts (e.g., sodium chloride) and other components of compositions utilized to treat contact lenses. For example, U.S. Pat. No. 4,438,011 (Howes) states that ionic species such as chloride inhibit the antimicrobial activity of the biguanide chlorhexidine, and teaches that the concentration of such ionic species must therefore be limited in order to maintain adequate antimicrobial activity for disinfecting contact lenses.

There is also a need for an improved means of preserving pharmaceutical compositions from microbial contamination. This need is particularly prevalent in the fields of ophthalmic and otic compositions. The antimicrobial agents utilized to preserve aqueous ophthalmic and otic compositions must be effective in preventing microbial contamination of the compositions when used at concentrations that are non-toxic to ophthalmic and otic tissues.

The present invention is directed to satisfying the above-cited needs.

SUMMARY OF THE INVENTION

The present invention is directed to certain aminobiguanides having antimicrobial activity and to pharmaceutical compositions containing one or more of these aminobiguanides to preserve the compositions from contamination by microorganisms. The invention is also directed to the use of the subject aminobiguanides to disinfect contact lenses.

The aminobiguanides of the present invention have excellent antimicrobial activity, even at very low concentrations. These compounds retain excellent antimicrobial activity, even in the presence of salt-containing media, such as saline solutions. The retention of antimicrobial activity in the presence of sodium chloride and other salts is highly significant, since such salts are commonly found in pharmaceutical compositions. For example, sodium chloride and other salts are frequently used to adjust the osmolality of ophthalmic compositions, so as to make the compositions isotonic with human tears. Sodium chloride or other salts may also be present in aqueous otic compositions. Moreover, compositions utilized to treat contact lenses frequently contain cleaning agents or other ingredients that may also have a negative effect on the activity of antimicrobial agents. The ability of the aminobiguanides of the present invention to retain a high level of antimicrobial activity, even in the presence of salts and other ingredients of pharmaceutical compositions, is therefore an important feature of the present invention.

DESCRIPTION OF PREFERRED EMBODIMENTS

The aminobiguanide compounds of the present invention have the following formula:

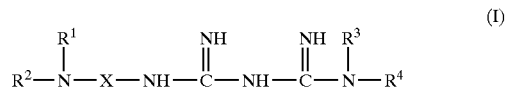

(I)

wherein:

$R^1$, $R^2$, $R^3$ and $R^4$ are the same or different and are selected from hydrogen, alkyl ($C_1$ to $C_{20}$), aminoalkyl ($C_1$ to $C_{20}$), aryl, arylalkyl ($C_3$ to $C_{20}$), aryloxyalkyl ($C_3$ to $C_{20}$) and cycloalkyl ($C_3$ to $C_{20}$); and X is alkyl ($C_2$ to $C_{20}$), optionally containing one or more substituents selected from the group consisting of cycloalkyl ($C_3$ to $C_{20}$), aryl, arylalkyl ($C_3$ to $C_{20}$) and aryloxyalkyl ($C_3$ to $C_{20}$).

In the foregoing definitions of the $R^1$, $R^2$, $R^3$, $R^4$ and X substituents, the alkyl groups may be saturated or unsaturated and may be in the form of either straight or branched chains, and all of the groups other than hydrogen may contain one or more heteroatoms. The compounds of the present invention also include pharmaceutically acceptable salts of the compounds of formula (I).

The preferred compounds of formula (I) are those wherein $R^1$, $R^2$, $R^3$ and $R^4$ are selected from the group consisting of hydrogen, alkyl ($C_1$ to $C_{20}$), aminoalkyl ($C_1$ to $C_{20}$) and cycloalkyl ($C_3$ to $C_{20}$), and X is selected from the group consisting of alkyl ($C_2$ to $C_{20}$) and alkyl ($C_2$ to $C_{20}$) substituted with one or more cycloalkyl ($C_3$ to $C_{20}$) groups.

The most preferred compounds are those wherein $R^1$, $R^2$, $R^3$ and $R^4$ are hydrogen or $C_1$ to $C_{20}$ alkyl, and X is $C_2$ to $C_{10}$ alkyl or $C_2$ to $C_{10}$ alkyl containing one or more cycloalkyl ($C_3$ to $C_{20}$) substituents. Examples of such compounds are set forth in the following table:

| Compound Number | $R^1$ | $R^2$ | $R^3$ | $R^4$ | X |
|---|---|---|---|---|---|
| 1 | $CH_3$ | $CH_3(CH_2)_{11}$ | H | 1,4-dimethylpentyl | $(CH_2)_3$ |
| 2 | $CH_3$ | $CH_3(CH_2)_{11}$ | H | heptyl | $(CH_2)_3$ |
| 3 | $CH_3$ | $CH_3(CH_2)_{11}$ | H | benzyl | $(CH_2)_3$ |
| 4 | $CH_3$ | $CH_3(CH_2)_{11}$ | H | decyl | $(CH_2)_3$ |
| 5 | $CH_3$ | $CH_3(CH_2)_{11}$ | H | N-methyl-N-dodecyl amino propyl | $(CH_2)_3$ |

The compound wherein X is propyl, $R^1$ is methyl, $R^2$ is dodecyl, $R^3$ is hydrogen and $R^4$ is 1,4-dimethylpentyl (i.e., Compound Number 1) is the most preferred compound for formula (I).

The compounds of formula (I) may be synthesized in accordance with the following reaction scheme:

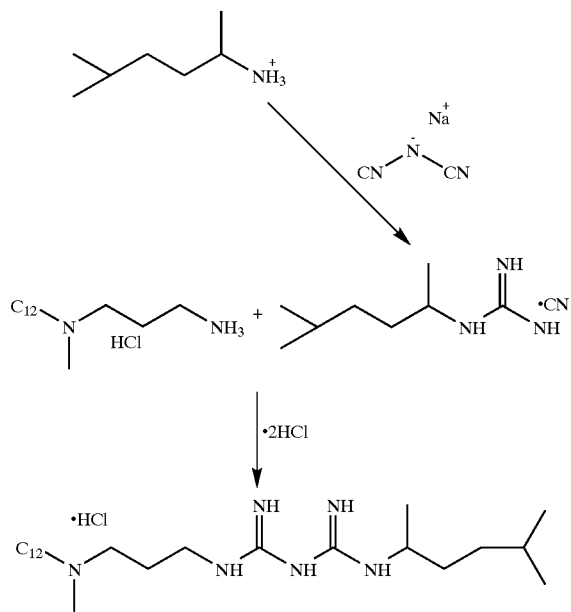

Suitable methods for synthesizing the compounds of formula (I) are further demonstrated by the following examples, which describe the synthesis of certain preferred compounds:

EXAMPLE 1
Synthesis of Compound Number 1:

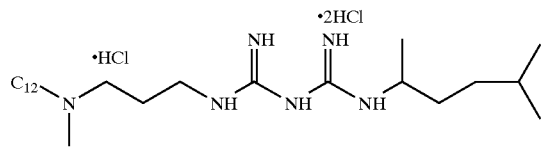

A mixture of 2,5-dimethylhexylamine hydrochloride (3 g. 19.9 mM) and 1.96 g (22 mM) of sodium dicyanamide in 30 ml of 1-butanol was reacted under reflux for 6 hours and concentrated in vacuo. This was suspended in 200 ml of water and extracted with chloroform (2×200 ml). The organic layer was washed with water and dried over $MgSO_4$ and concentrated in vacuo. This residue was crystallized from ethyl acetate-n-hexane to yield 3.0 g. (75% yield). Nmr ($CDCl_3$) δ 5.3 (m, 3H), 3.6 (m, 1H)), 1.6 (s, 3H), 1.6–1.4 (m, 3H), 1.3 (m, 5H), and 0.9 (d, 6). This material used without further purification. To a pressure bottle added 8.0 g (24.3 mM) of N,N-dodecylmethyl-1,3-propanediamine dihydrochloride, 6.23 g (34.4 mM) of 1,4-dimethylpentylcyanoguanidine and 1.5 mL of amyl alcohol. The bottle was sealed and heated to 150° C. Melting began at about 110° C. and the reaction mixture was stirred at 150° C. for 4 hrs. after which ethanol was added to dissolve the material. This material was acidified with concentrated HCl to pH 0–1 and precipitated with acetone to yield white material. This was crystallized from isopropanol-acetone to give the desired compound as a white crystal. Elemental Analysis: Calcd. for $C_{25}H_{57}N_6Cl_3$(549.14): C, 54,68; H, 10.65; N, 15.31; Cl, 19.37 Found: C, 55.06; H 10.44; N, 15.14; Cl, 19.10. Nmr (DMSO-d6): δ 3.7 (m, 1H), 3.3 (m, 4H), 3.0 (m, 2H), 2.8 (s, 3H, N—$CH_3$), 2.1 (b. 2H), 1.8 (b, 2H), 1.5 (b, 2H), 1.3 (m, 21H),and 0.9 (d, 6H, $CH_3$). LC/MS also confirmed the above structure.

EXAMPLE 2
Synthesis of Compound Number 2:

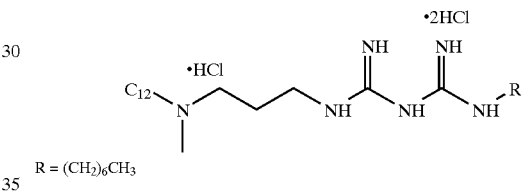

R = $(CH_2)_6CH_3$

By following the procedure described in the synthesis of Compound 1 (see Example 1, above) with a mixture of 0.658 g (0.658 g., 2 mM) of N,N-dodecylmethyl-1,3-propanediamine dihydrochlorides and 0.346 g (2 mM) of n-hexylcyanoguanidine, 0.5 g (49% yield) of the desired product was obtained. Elemental Analysis: Calcd. for $C_{25}H_{58}N_6Cl_3$: C, 54.68; H, 10.65; N, 15.31; Cl, 19,37 Found:, C, 54.71; H, 10.26; N, 15.29; Cl; 19.19 Nmr (DMSO-d6): δ 3.4–2.9 (m, 8H), 2.7(s, 3H, N—CH3), 1.9 (b, 2H), 1.7 (b, 2H), 1.5 (b, $NHCH_2CH_2$, 2H), 1.3. (app. s, 26H), and 0.9 (t, 3H, $CH_3$).

EXAMPLE 3
Synthesis of Compound Number 3:

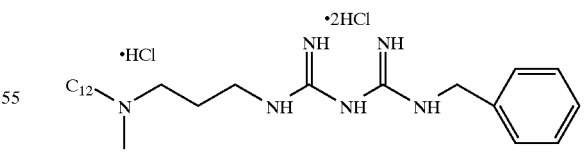

14.3 g (0.1 M) of benzylamine hydrochloride was reacted with 8.9 g (0.1 M) of sodium dicyanamide in 100 ml of n-butanol at 150° C. for 5 hrs. and treated with 50 ml of water. The collected organic layer was washed with 0.1N HCl (2×50 ml) and water (1×50 ml) consequently and concentrated in vacuo to leave a viscous material which was taken up by ethyl acetate. This was dried over $MgSO_4$ and crystallized from ethylacetate-hexane to afford 13 g (75% yield). m.p. 95–100° C. Without further purification, this was used for the next reaction. By following the same procedure as described in the synthesis of Compound 1, with 0.987 g (3 mM) of N,N-dodecylmethyl-1,3-propanediamine dihydrochlorides and 0.678 g (3.9 mmol) of the above cyanoguanidine, the desired compound was obtained. Elemental Analysis: Calcd. for $C_{25}H_{49}N_6Cl_3$: C, 55.60; H, 9.14; N, 15.56; Cl 19.69 Found: C, 55.32; H, 9.25; N, 15.53; C, 19.36. Nmr. (DMSO-$d_6$) δ 7.35 (app. s, $C_6H_5$, 5H), 4.4 (s, 2H $CH_2C_6H_5$), 3.2 (t, 2H), 3.0 (broad, 4H), 2.7 (s, 3H, N—$CH_3$), 1.9 (m, 2H), 1.6 (t, 3H), 1.3 (app. s, 18H), and 0.9 (t, 3H, $CH_3$—$CH_2$).

EXAMPLE 4
Synthesis of Compound Number 4:

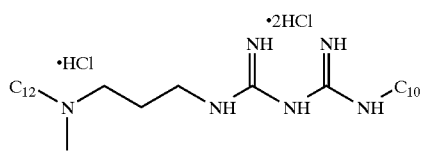

The same procedure as described in the synthesis of Compound 1 (see Example 1, above) was utilized with 0.73 g (2.2 mM) of N,N-dodecylmethyl-1,3-propanediamine dihydrochlorides and 0.5 g (2.2 mM) of decylcyanoguanidine to afford 0.5 g (38.6%) of the desired product. Elemental analysis: Calcd. for $C_{28}H_{63}N_6Cl_3$ (590.20): C, 56.98; H, 10.76; N, 14.24; Cl, 18.02 Found: C, 56.68; H, 10.62; N, 14.19; Cl, 17.85 Nmr. (CDCl$_3$) δ 2.9 (N—$CH_3$), 2.3 (broad, 2H), 1.9 (broad, 2H), 1.7 (broad, 2H) 1.5 (s, 32H), and 1.1 (t, 6H).

EXAMPLE 5
Synthesis of Compound Number 5:

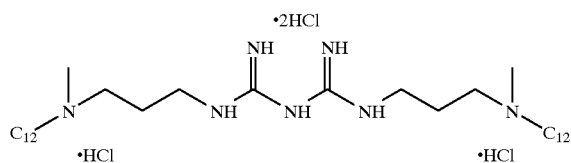

A mixture of N,N-dodecylmethyl-1,3-propanediamine dihydrochloride (2.0 g. 6.1 mM) and 0.7 g (7.9 mM) of sodiumdicyanamide was reacted in 40 ml n-butanol under reflux for 5 hrs and aqueous NaHCO$_3$ was added. The organic layer was separated and dissolved in chloroform solution. This chloroform solution was washed with aqueous NaHCO$_3$ and water successively and concentrated in vacuo. This residue was crystallized from methanol. m.p. 80–81. Elemental Analysis: Calcd. for $C_{18}H_{37}N_5$ (323.53) C, 66.83; H, 11.53; N, 21.65 Found: C, 66.39; H, 11.51; N, 21.71. Nmr (CD$_3$OD) δ 3.2 (t, 2H), 2.4 (m, 4H), 2.2 (s, 3, N—CH3), 1.7 (m, 2H), 1.5 (m, 2H), 1.3 (s, 18H), and 0.9 (t, 3H). This cyanoguanidine (0.5 g, 1.5 mM) was reacted with 0.51 g (1.5 mM) of dihydrochloride salt of N,N-dodecylmethyl-1,3-propanediamine in 0.5 ml of amylalcohol at 155° C. for 3 hrs and precipitated with acetone. The precipitate was dissolved in ethanol and adjusted to pH 1.0 with HCl. This was concentrated in vacuo and crystallized from ethanol to afford 0.71 g. (70% yield). Elemental analysis: Calcd. for $C_{34}H_{73}N_7$·4HCl (726.26): C, 56.23; H, 10.69; N, 13.56; Cl 19.53 Found: C, 55.86; H, 10.30; N, 13.71; Cl, 19.20. LC/MS confirmed the above structure. Nmr (DMSO-$d_6$) δ 3.3–2.9 (m, 12H), 2.7 (s, 6H, NCH$_3$), 1.9 (b, 4H), 1.6 (b, 4H), 1.3 (s, 36H), and 0.8 (t, 6H, CH$_3$).

The compounds of formula (I) can be used individually, in combination with one or more other compounds of formula (I), or in combination with other disinfectants or preservatives. The compounds may, for example, be used in combination with the polymeric quaternary ammonium compounds described in U.S. Pat. No. 4,407,791; the entire contents of that patent are hereby incorporated in the present specification by reference. As described in the '791 patent, those polymeric quaternary ammonium compounds are useful in disinfecting contact lenses and preserving ophthalmic compositions. The most preferred polymeric quaternary ammonium compound is polyquaternium-1. Such polymeric quaternary ammonium compounds are typically utilized in an amount of from about 0.0001 to 0.01 percent weight/volume ("w/v %"). For the agent polyquaternium-1, a concentration of 0.001 w/v % is preferred.

The amount of each compound used will depend on the purpose of the use, e.g., disinfection of contact lenses or preservation of pharmaceutical compositions, and the absence or inclusion of other antimicrobial agents. The concentrations determined to be necessary for the above-stated purposes can be functionally described as "an amount effective to disinfect" and "an amount effective to preserve" or variations thereof. The concentrations used for disinfection will generally be in the range of from about 0.0001 to about 0.1 percent w/v % ("w/v %"). The concentrations used for preservation will generally be in the range of from about 0.00001 to about 0.01 w/v %.

The compositions of the present invention may be aqueous or nonaqueous, but will generally be aqueous. As will be appreciated by those skilled in the art, the compositions may contain a wide variety of ingredients, such as tonicity agents (e.g., sodium chloride or mannitol), surfactants (e.g., polyvinyl pyrrolidone and polyoxyethylene/polyoxypropylene copolymers), viscosity adjusting agents (e.g., hydroxypropyl methyl cellulose and other cellulose derivatives) and buffering agents (e.g., borates, citrates, phosphates and carbonates). As indicated above, the ability of the compounds of formula (I) to retain their antimicrobial activity in the presence of such agents is a significant advantage of the present invention.

The ophthalmic compositions of the present invention will be formulated so as to be compatible with the eye and/or contact lenses to be treated with the compositions. As will be appreciated by those skilled in the art, the ophthalmic compositions intended for direct application to the eye will be formulated so as to have a pH and tonicity that are compatible with the eye. This will normally require a buffer to maintain the pH of the composition at or near physiologic pH (i.e., 7.4) and may require a tonicity-adjusting agent (e.g., NaCl) to bring the osmolality of the composition to a level that ranges from slightly hypotonic to isotonic, relative to human tears. This range corresponds to an osmolality of from about 220 to about 320 milliosmoles per kilogram water ("mOsm/kg").

The formulation of compositions for treating contact lenses (e.g., disinfecting and/or cleaning) will involve similar considerations, as well as considerations relating to the physical effect of the compositions on contact lens materials and the potential for binding or absorption of the components of the composition by the lens. The contact lens disinfecting compositions of the present invention will preferably be formulated as aqueous solutions, but may also be formulated as nonaqueous solutions, as well as suspensions, gels, and so on. The compositions may contain a variety of tonicity agents, surfactants, viscosity adjusting agents and buffering agents, as described above.

The above-described compositions may be used to disinfect contact lenses in accordance with processes known to those skilled in the art. More specifically, the lenses will first be removed from the eyes of the patients, and then will be immersed in the compositions for a time sufficient to disinfect the lenses. This immersion will typically be accomplished by means of soaking the lenses in a solution overnight (i.e., approximately six to eight hours). The lenses will then be rinsed and placed in the eye. Prior to immersion in the disinfecting compositions, the lenses will preferably also be cleaned and rinsed.

The compositions and methods of the present invention may be used in conjunction with various types of contact lenses, including both lenses generally classified as "hard" and lenses generally classified as "soft".

The compounds of formula (I) may also be included in various types of pharmaceutical compositions as preservatives, so as to prevent microbial contamination of the compositions. The types of compositions which may be preserved by the compounds of formula (I) include: ophthalmic pharmaceutical compositions, such as topical compositions used in the treatment of glaucoma, infections, allergies or inflammation; otic pharmaceutical compositions, such as topical compositions used in the treatment of bacterial infections or inflammation of the ear; compositions for treating contact lenses, such as cleaning products and products for enhancing the ocular comfort of patients wearing contact lenses; other types of ophthalmic compositions, such as ocular lubricating products, artificial tears, astringents, and so on; dermatological compositions, such as antiinflammatory compositions, as well as shampoos and other cosmetic compositions; and various other types of pharmaceutical compositions.

The present invention is not limited with respect to the types of pharmaceutical compositions in which the compounds of formula (I) may be contained as preservatives, but the compounds are particularly useful in preserving ophthalmic and otic compositions from microbial contamination. The compounds are particularly useful in these types of compositions due to the ability of the compounds to exhibit a preservative effect at very low concentrations, without adversely affecting ophthalmic and otic tissues.

The following examples are provided to further illustrate the use of the compounds of formula (I) in pharmaceutical compositions and to demonstrate the antimicrobial activity of the compounds.

EXAMPLE 6

The following formulation represents an example of a contact lens disinfecting solution of the present invention. In this formulation, the aminobiguanide compounds of the present invention function to preserve the formulation from microbial contamination during storage. The compounds also function as an active disinfecting agent when the formulation is applied to contact lenses.

| Ingredient | Concentration (w/v %) |
|---|---|
| Compound | 0.0005 |
| Sorbitol | 1.2 |
| AMP-95 ™ | 0.45 |
| Sodium Citrate | 0.65 |
| Sodium Chloride | 0.1 |
| Boric Acid | 0.6 |
| EDTA | 0.05 |
| Tetronic 1304 ™ | 0.05 |
| Purified Water | q.s. 100 |
| HCl/NaOH | q.s. pH 7.8 |

In the foregoing formulation, the term "Compound" is intended to represent any of the aminobiguanides of formula (I). The formulation is an aqueous, isotonic solution. The solution can be prepared by sequentially dissolving each ingredient in water, and adjusting the pH of the resulting solution, if necessary.

EXAMPLE 7

The following formulation represents another example of a contact lens disinfecting solution of the present invention:

| Ingredient | Concentration (w/v %) |
|---|---|
| Compound | 0.001 |
| Boric Acid | 0.58 |
| Sodium Borate | 0.18 |
| Disodium EDTA | 0.05 |
| Sodium Chloride | 0.49 |
| Purified Water | q.s. 100 |
| NaOH/HCl | q.s. pH 7.0 |

The foregoing formulation is an aqueous, isotonic solution. It can be prepared in the same manner as the solution of Example 6 above.

EXAMPLE 8

The antimicrobial activity of the solution of Example 6, containing 0.0005 w/v % of the aminobiguanide identified above as Compound No. 1, was evaluated relative to three key microorganisms. The evaluation was conducted by determining the extent to which the solution reduced an initial population of about $10^6$/mL microorganisms over time. The results were as follows:

| Microorganism | $Log_{10}$ Reduction at 6 hours | $Log_{10}$ Reduction at 24 hours |
|---|---|---|
| Candida albicans | 2.1 | 5.0 |
| Serratia marcescens | 3.9 | 6.1 |
| Staphlococcus aureus | 3.7 | 4.9 |

These results demonstrate that the aminobiguanides of formula (I) have potent antimicrobial activity.

EXAMPLE 9

The antimicrobial activity of the solution of Example 7, containing 0.0005 w/v % of Compound No. 1, was also evaluated using essentially the same procedure as those described in Example 8 above. The results were as follows:

| Microorganism | Log10 Reduction at 6 hours | Log10 Reduction at 24 hours |
| --- | --- | --- |
| Candida albicans | 1.4 | 4.0 |
| Serratia marcescens | 3.0 | 4.8 |
| Staphlococcus aureus | 3.4 | 4.6 |

These results further demonstrate the potent antimicrobial activity of the aminobiguanides of the present invention.

EXAMPLE 10

The antimicrobial activity of Compound No. 1 at a concentration of 0.0005 w/v % in water was also evaluated. The results were as follows:

| Microorganism | Log10 Reduction at 6 hours | Log10 Reduction at 24 hours |
| --- | --- | --- |
| Candida albicans | 2.1 | 3.8 |
| Serratia marcescens | 5.5 | 3.9 |
| Staphylococcus aureus | 4.1 | 6.0 |

These results demonstrate that the antimicrobial activity of the solutions tested in Examples 8 and 9 above is attributable to the aminobiguanide of the present invention (i.e., Compound No. 1), rather than other components of the solutions.

A comparison of the activity of Compound No. 1 when contained in a distilled water vehicle to the activity of Compound No. 1 when contained in buffered, isotonic solutions shows that the aminobiguanides of the present invention retain their antimicrobial activity when utilized in the presence of sodium chloride and other excipients commonly contained in pharmaceutical compositions. This retention of activity is apparent from a comparison of the antimicrobial activity demonstrated in Examples 8 and 9 with the antimicrobial activity demonstrated in Example 10.

What is claimed is:

1. A compound of the following formula:

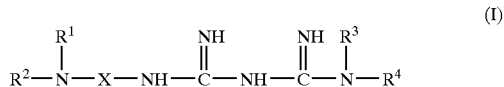

wherein:

R$^1$ is selected from the group consisting of alkyl (C$_1$ to C$_{20}$), aminoalkyl (C$_1$ to C$_{20}$) and cycloalkyl (C$_3$ to C$_{20}$);

R$^2$ and R$^3$ are the same or different and are selected from the group consisting of hydrogen, alkyl (C$_1$ to C$_{20}$), aminoalkyl (C$_1$ to C$_{20}$) and cycloalkyl (C$_3$ to C$_{20}$);

R$^4$ is selected from the group consisting of alkyl (C$_1$ to C$_{20}$), aminoalkyl (C$_1$ to C$_{20}$) and cycloalkyl (C$_3$ to C$_{20}$); and X is selected from the group consisting of alkyl (C$_2$ to C$_{10}$) and alkyl (C$_2$ to C$_{10}$) substituted with cycloalkyl (C$_3$ to C$_{20}$);

or a pharmaceutically acceptable salt thereof.

2. A compound according to claim 1, wherein R$^1$ is alkyl (C$_1$ to C$_{20}$), and R$^2$ and R$^3$ are selected from the group consisting of hydrogen and alkyl (C$_1$ to C$_{20}$).

3. A compound according to claim 1, wherein X is propyl, R$^1$ is methyl, R$^2$ is dodecyl, R$^3$ is hydrogen, and R$^4$ is selected from the group consisting of 1,4-dimethylpentyl, heptyl, decyl and N-methyl-N-dodecyl amino propyl.

4. A compound according to claim 1, wherein R$^1$ is methyl, R$^2$ is dodecyl, R$^3$ is hydrogen, R$^4$ is 1,4-dimethylpentyl, and X is propyl.

* * * * *